United States Patent [19]

Richey et al.

[11] 4,304,999

[45] Dec. 8, 1981

[54] ECCENTRIC SOURCE COLLIMATOR ASSEMBLY FOR ROTATING SOURCE CT SCANNER

[75] Inventors: Joseph B. Richey, Shaker Heights; John J. Kuwik, Hudson; Arthur B. Braden, Solon; Samuel K. Taylor, Chardon; John Covic, Wickliffe, all of Ohio

[73] Assignee: Technicare Corporation, Cleveland, Ohio

[21] Appl. No.: 192

[22] Filed: Jan. 2, 1979

[51] Int. Cl.³ .......................... A61B 6/00; G02B 5/00
[52] U.S. Cl. .................................. 250/445 T; 250/505
[58] Field of Search ................... 250/445 T, 360, 505, 250/508, 509, 510

[56] References Cited

U.S. PATENT DOCUMENTS

| | | | |
|---|---|---|---|
| 4,096,389 | 6/1978 | Ashe et al. | 250/505 |
| 4,101,768 | 7/1978 | Lill | 250/360 |
| 4,132,895 | 1/1979 | Froggatt | 350/505 |

*Primary Examiner*—Alfred E. Smith
*Assistant Examiner*—T. N. Grigsby
*Attorney, Agent, or Firm*—Fay & Sharpe

[57] ABSTRACT

Disclosed is a collimator for a tomographic scanner which performs the collimator function of dividing a fan of radiation into a multiplicity of finger beams and the attenuator function of causing a generally bell-shaped radiation energy distribution across a scan circle. The collimator has larger effective apertures for forming radiation into finger beams to traverse the center of the scan circle than for forming finger beams to traverse the edges of the scan circle. The width of the collimator apertures are defined by radially oriented vanes arranged along a circular arc. By offsetting the radiation source from the geometric center of the circular arc, the vanes defining the width of some apertures are more skewed than others relative to the radiation paths.

27 Claims, 13 Drawing Figures

ECCENTRIC SOURCE COLLIMATOR ASSEMBLY FOR ROTATING SOURCE CT SCANNER

BACKGROUND OF THE INVENTION

The invention relates generally to the field of radiation imaging of internal structures and, more specifically, to computerized axial tomographic (CT) X-ray scanners. Unlike conventional exposed film X-ray apparatus, the CT scanner produces narrow beams of radiation, either X-ray or gamma rays, through plural coplanar paths defining a cross-sectional or tomographic view of the patient's internal organs, such as the brain. The attenuated beams are sensed by radiation detectors whose electrical output is indicative of the intensity of the radiation received by the detector. One of the early types of CT scanners referenced in the patent literature is shown, for example, in Hounsfield U.S. Pat. No. 3,778,614. This system is generally referred to in the art as the "translate and rotate" system. A source and a single detector, for example, are aligned opposite each other on a mechanism which causes the beam path between the source and detector to move laterally across the scan circle. After rotating the source/detector carriage assembly to a new orientation, the translational scan is repeated. Readings are taken at uniformly spaced parallel beam locations and representative values are digitally stored. Data from a full set of scans involving numerous relocations of the beam path is manipulated according to known mathematics involving "back projection" to arrive at a digital representation of the tomographic image. This digital representation is converted to a tomogram which can be viewed on a cathode ray tube. Ohio-Nuclear, Inc. markets a type of translate and rotate computerized tomographic scanner under the trademark "DELTA SCAN".

The major disadvantage of the translate and rotate system is slowness of the scan mechanism due to the different alternating types of motion. The major advantages of the translate and rotate system are due to the fact that a single detector scans across the entire scan circle thus enabling sampling at any time and avoiding the need to have matched detectors or gain matching.

Another type of scan technique called "purely rotational" employs a fan beam source with a subtended detector array in a fixed relationship such that the fan beam and detector array rotate with each other. This system has a major disadvantage. Numerous detectors are required and none scans across the entire patient. Thus, the sampling resolution is lowered and gain matching of the detectors is required. The major advantage of the purely rotational system is its high scanning speed. The high speed of the scanning motion is desirable to avoid the effect on the image of the resultant displacement of organs due to a patient's breathing.

It has been found that computer image reconstruction can be accomplished with yet another arrangement of source and detectors. In this new system, the detector array is a stationary arc of uniformly spaced detectors about the center point in the scan circle. The fan pattern source revolves about the center point inside the detector array irradiating the scan circle and subtending at any given time only a fraction of the detectors in the total array. If desired, the array may be a complete circle or ring. The reconstruction algorithms are described in Lakshminarayanan, "Reconstruction from Divergent Ray Data", Technical Report No. 92, State University of New York at Buffalo, Computer Sciences Department, January, 1975.

The new type of scanning system, although requiring numerous detectors and somewhat more elaborate digital processing for reconstructing an image, provides the advantage of high scanning speed due to the single mechanical motion for rotation while also providing the capability of achieving high sampling resolution and avoiding gain matching requirements because each detector views the source across the entire scan circle.

If the circular array of detectors does not fully encircle the patient, it is possible for the patient to be exposed to unused radiation when the source approaches the terminus of its orbit and part of the fan pattern falls outside the detector array. Another problem is presented when the detectors are spaced apart throughout the array since the fan pattern is not aligned with specific detectors but instead floods the scan circle. In this case, a portion of the radiation falls between adjacent detectors and is not used for data collection. This radiation dosage is received by the patient, however, even though it is not used.

In the above three types of scanning systems, it has been found that reconstruction is more easily and accurately accomplished if the distribution of the amount of the radiation traversing the scan circle is generally a bell-shaped distribution with its peak corresponding to radiation traversing the center of the scan circle and its edges corresponding to radiation traversing the scan circle nearly tangential to the scan circle. To modify the amount of radiation attenuating filters, such as blocks of aluminum which are machined-thin near the center and thick near the edges, are inserted between the source of radiation and the detectors. See U.S. Pat. No. 3,937,963. Other shaped attenuation filters which better match the radiation distribution with the anticipated amount of attenuation along various paths through the scan circle are shown in U.S. Pat. No. 3,755,672.

SUMMARY OF THE INVENTION

The purpose of the invention is to reduce the dosage of unused radiation which the patient receives. This is accomplished by dividing a fan pattern into a plurality of discrete diverging beams and keeping them trained on respective detectors for as long as each traverse the scan circle. Unnecessary dosage further is reduced by employing an eclipsing shutter mechanism to limit the portion of a fan pattern of radiation passing through the scan circle at all times to a width coincident with the subtended portion of the detector array.

Further reductions in dosage are achieved by collimating beams in such a manner that a generally bell-shaped energy distribution is produced without an attenuating filter. Specifically, the collimator defines smaller beams to traverse near the edges of the scan circle and larger beams to traverse near the center of the scan circle.

In one embodiment, the invention is implemented by skewing collimator vanes relative to the source such that the effective opening of apertures defining beams near the center of the scan circle is larger than the effective opening of apertures defining beams more nearly tangential to the scan circle. In another embodiment, the apertures are wider near the center of the collimator and narrower near the edges.

In a preferred embodiment the collimator is combined with a rotating shutter for a computerized tomographic scanner in which the source rotates and a series of detectors is spaced about the center of rotation coplanar with the orbit of the source. A radiation shield restricts the radiation from the source to a solid fan pattern aimed so that the extremes of the fan are tangential to the scan circle. An eclipsing shutter mechanism about the source restricts the fan pattern at all times to a pattern which will fall on the detector array as the source traverses its orbital path. The shutter mechanism includes a multi-apertured collimator, with one aperture for each detector, for training each one of the discrete beams collectively defining the fan pattern on a specific detector for as long as each beam intersects the scan circle. The shutter mechanism is responsive to rotation of the source which causes a specific fractional amount of rotation in the opposite direction as the source moves. The respective collimator apertures keep themselves aligned between the source and their respective detectors through the scan circle. The source is eccentrically positioned relative to the rotating collimator in such a manner that the amount of radiation in the collimated beams varies across the scan circle. In the preferred embodiment, the means for rotating the shutter mechanism is an epicyclic gear train, although other means are possible such as a.d.c. motor servo drive, or the like.

DESCRIPTION OF THE PREFERRED EMBODIMENTS

Figure 1:
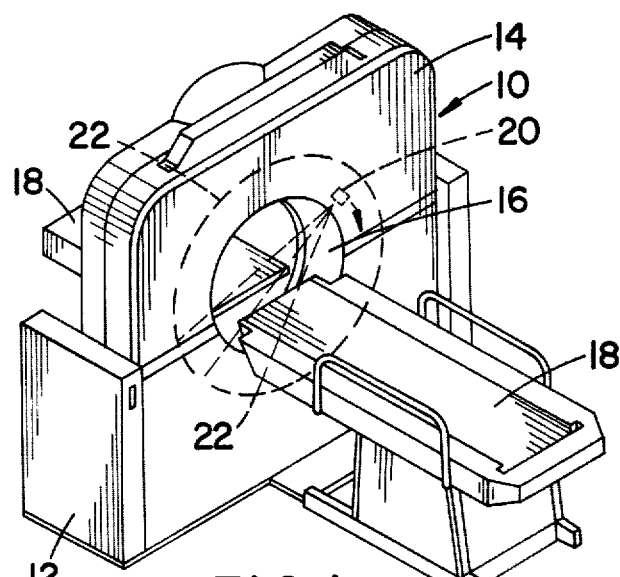
FIG. 1 is a perspective view of CT scanner apparatus associated with the invention.

FIG. 1 illustrates the mechanical apparatus associated with the rotation source type CT scanner system. A gantry assembly 10 includes a U-shaped frame 12 pivotally supporting a gantry 14 having a central circular opening 16 through which a patient is inserted for a body scan, for example, on a two-piece patient table 18. Shown in phantom, a source assembly 20 produces radiation in a coplanar fan pattern directed towards the opposite side of the opening 16 and intersecting the center of the opening 16. Mechanisms within the gantry 14 rotate the source assembly 20 clockwise about an axis through the center of the opening 16 perpendicular to the fan pattern. A ring of detectors 22, also shown in phantom in FIG. 1 is disposed within the gantry 14 concentrically to the opening 16 and at a somewhat greater radius from the center of the opening 16 than the source assembly 20. The ring of detectors 22 lies in the same plane as the fan pattern. The signals produced by detectors which are within the fan pattern are applied to a number of respective signal processing channels. By using the reconstruction processing system described in the copending application Ser. No. 838,084, entitled "X-ray Tomographic Apparatus", filed Sept. 30, 1977 and assigned to the assignee of the present application, the number of detectors in the detector ring can be reduced to the number of detectors which subtends 180° plus the angle of a detector fan. In the preferred embodiment the detectors subtend about 212°. The copending application is incorporated by reference herein.

Figure 2:
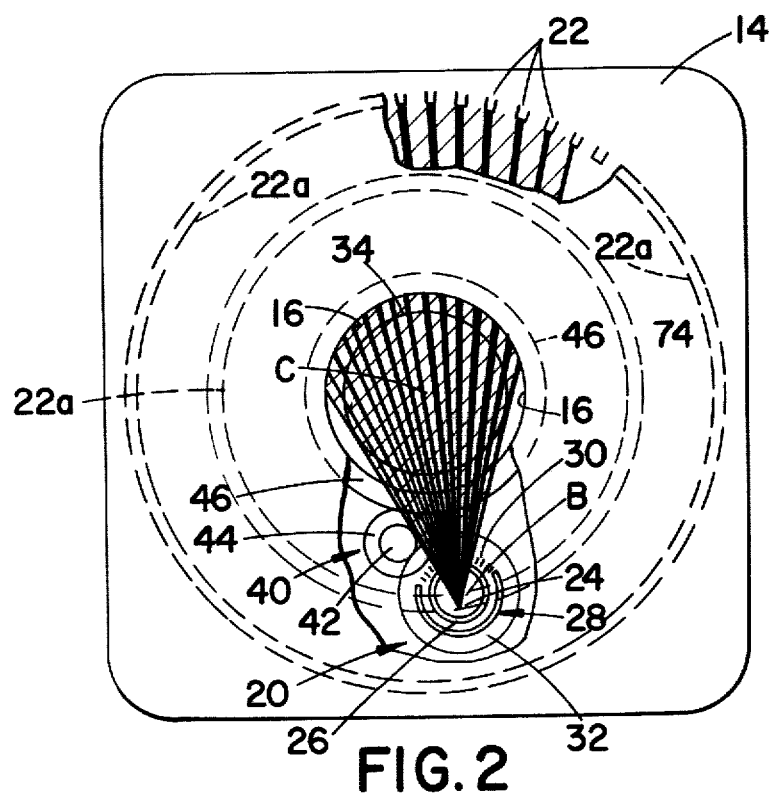
FIG. 2 is a plan view of the gantry with portions broken away to expose the epicyclic gear train driving the collimator and shutter mechanisms.

In FIG. 2, the view of the gantry 14 shows the source assembly 20 at a low point on its orbit through circular path 20a. The source assembly 20 includes a source 24 and a radiation shield 26 therearound having a sector missing which causes the radiation directed toward the opening 16 to assume a fan shape. The thickness of the fan in the direction orthogonal to the paper may be slightly divergent and at the center of rotation C represents the thickness of the slice or tomograms to be reconstructed. Between the source 24 and the opening 16 is a shutter mechanism 28 having a section 30 which defines a series of very closely spaced apertures. Shutter mechanism 28 is eccentric about source 24 and is mounted for rotation on a planetary gear 32 about an axis B at the geometric center of shutter 28.

The source 24 with shield 26 produces a fan pattern of radiation whose angular width determines the diameter of a patient scan circle 34 at a given distance from the center of the scan circle. The scan circle 34 includes the area common to the fan at different positions of the source assembly 20 along its orbit 20a. The area within the scan circle is the area which the reconstructed image will represent. Thus, this area is selected to coincide with the portion of the patient's body, for example, the head of which a tomographic image is to be produced.

The angular size of the section 30 of closely space apertures in the shutter mechanism 28 is dependent upon the number and spacing of detectors 22. However, the arc spanned by the section 30 in the shutter mechanism is less than the arc spanned by the array of detectors 22. For example, if there are 424 detectors with half-degree spacing from the center line of one detector to the center line of the next detector, they cover an arc of 212° on the detector ring 22a. In the embodiment illustrated in FIG. 2, the resulting arc spanned by section 30 in the shutter mechanism has 424 apertures and is substantially 69% of the arc spanned by the detector array, i.e. 146.3°.

An alternate embodiment of the shutter mechanism is illustrated in FIGS. 3 and 5-7 in which like elements are shown with like reference numerals followed by a prime. In this embodiment, the collimator apertures have been replaced with a single large aperture and the radiation source is centered in shutter 28. The eclipsing shutter mechanism is explained in terms of these Figures.

Figure 4:
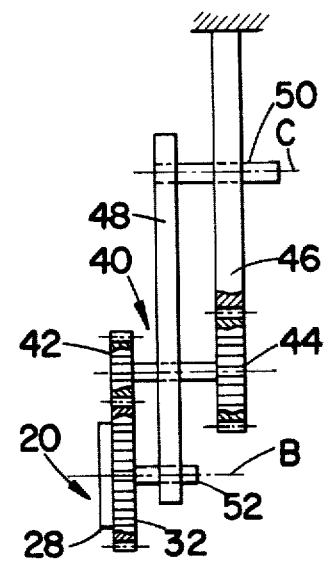
FIG. 4 is a side schematic detail view of the epicyclic gear train.
Figure 3:
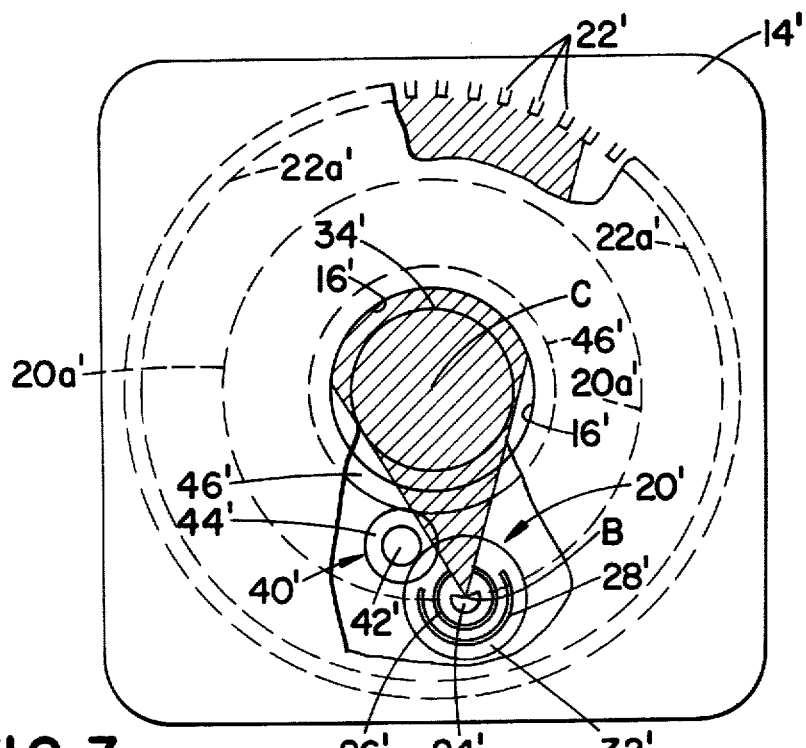
FIG. 3 is a plan view of an alternate embodiment of the gantry with portions broken away to expose the epicyclic gear train driving the shutter mechanism.

With reference to FIGS. 2, 3 and 4, a compound gear 40 is used to drive a planetary gear 32 on which the shutter 28 is arranged. Compound gear 40 includes a smaller spur gear 42 driving the planetary gear 32 and a larger spur gear 44, connected for rotation with smaller gear 42, engaging a stationary ring-shaped sun gear 46 affixed to the gantry and concentric with the scan circle about center c. As the source assembly 20 orbits in a clockwise direction along its path 20a, the compound drive gear 40 is caused to rotate clockwise which in turn causes the planetary gear 22 and shutter 28 to rotate counterclockwise. As shown in FIG. 4 in schematic form the axes of the gears are all fixed with respect to each other. For purposes of illustration, this is indicated by an imaginary arm 48 of FIG. 4 which is journalled at one end to an imaginary axle 50 of the sun gear 46 coinciding with the center c of the scan circle and intermediate its length with the common axle of the compound gear 4 and at the other end to an axle 52 at the geometric center B of the planetary gear 32. Because the sun gear is fixed, the arm 48 is free to rotate about the imaginary axle 50. This rotation produces the orbit of the source assembly 20 which is mounted on axel 52 such that it always faces center c. This motion is analogous to a sun, planet and moon system in which the sun gear 46 represents the sun, the source assembly 20 represents the planet and a fixed point on the planetary gear 32, for instance, the aperture in the shutter mechanism 28 represents the moon.

Figure 5:
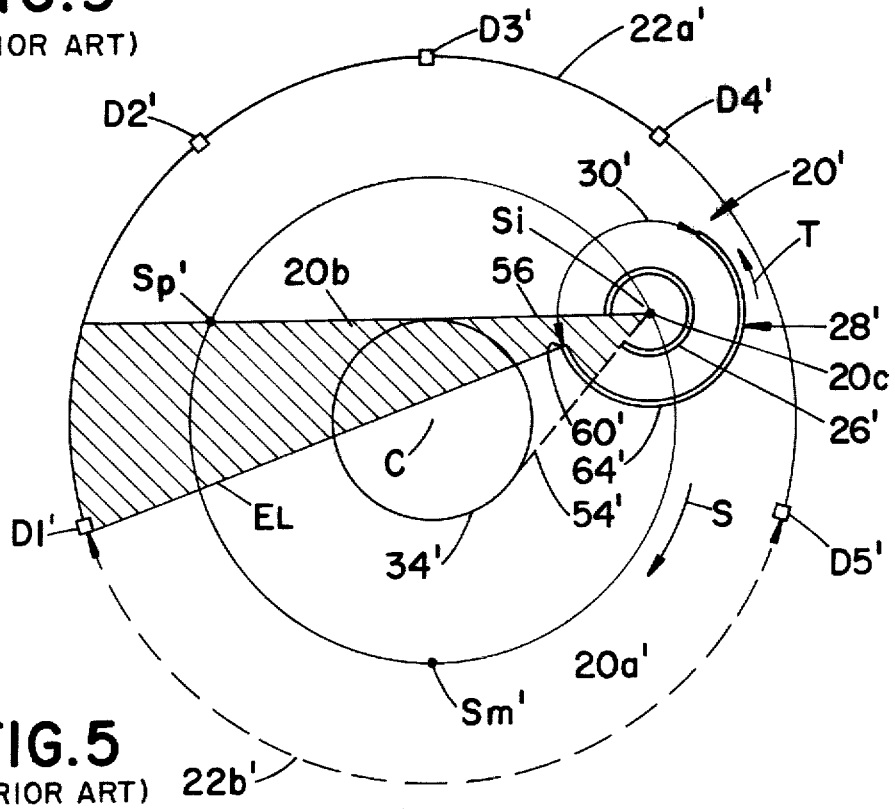
FIGS. 5, 6 and 7 are schematic representations of the relative position of the source, shutter mechanism, radiation fan pattern and detectors at three different source orientations.
Figure 6:
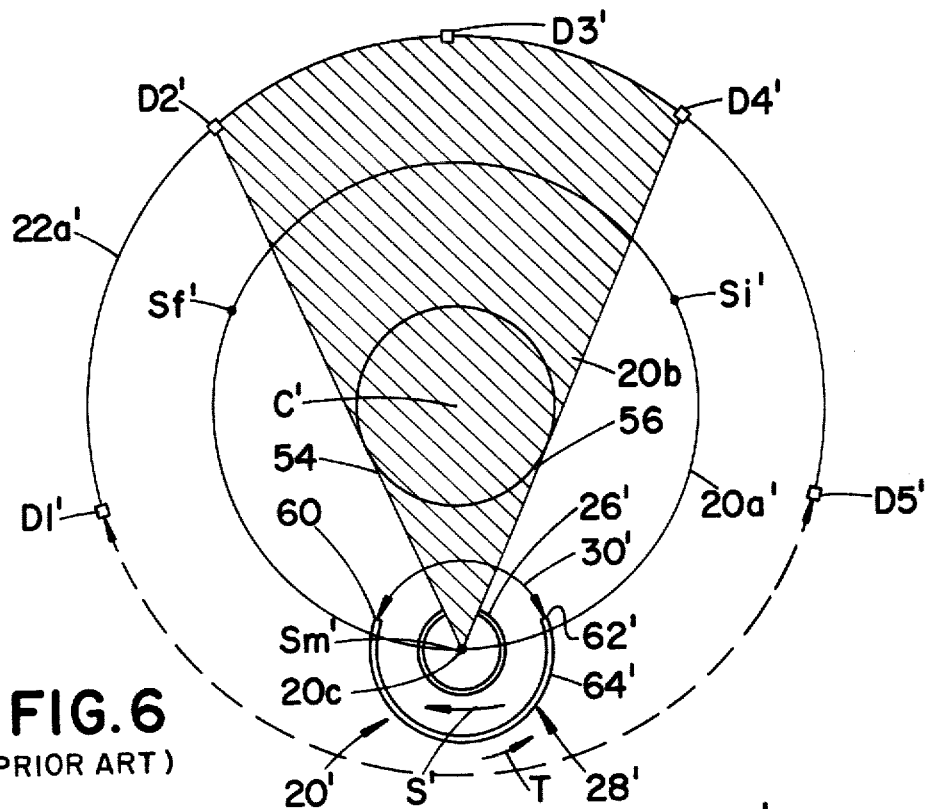
Figure 7:
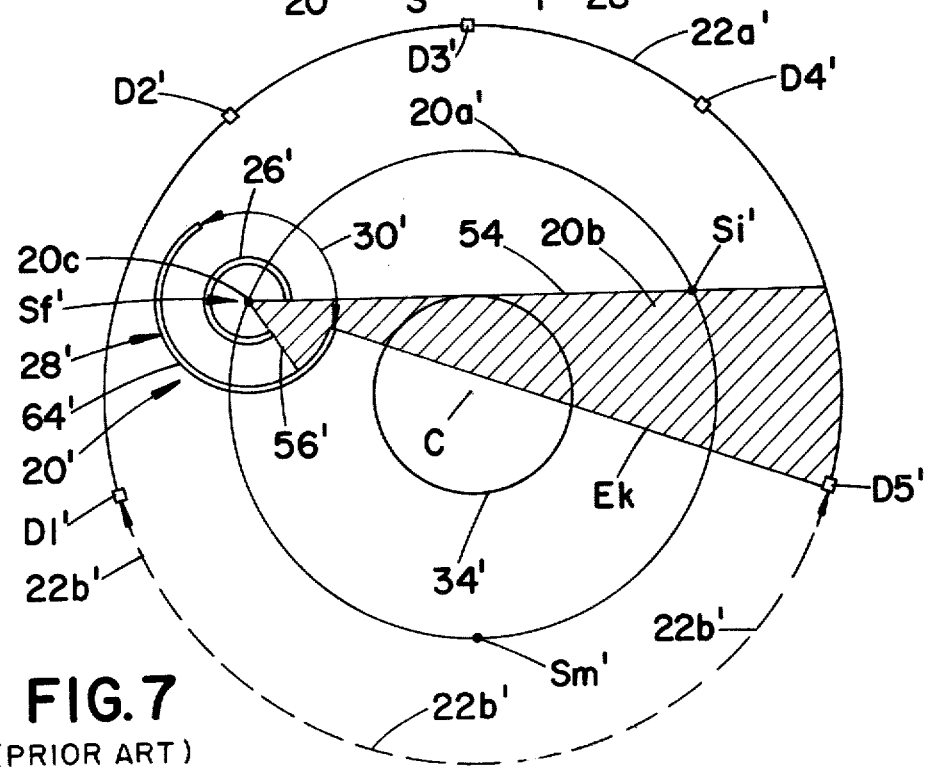

The requirement for this type of motion between the shutter mechanism and the source is demonstrated in FIGS. 5, 6 and 7 showing progressive clockwise orientations of the source. In FIG. 5, the source is shown at the initial point $S_i'$ of the scan cycle. In FIGS. 6 and 7, the source is shown at the midpoint $S_m'$ of the scan cycle and at the final or endpoint $S_f'$ of the scan cycle, respectively. FIGS. 5, 6 and 7 also show detector ring 22' and, for illustration, the first, last and three intermediate stationary detectors D1', D2', D3', D4' and D5' in the ring. Of course, in the practical embodiment there are many detectors in the spaces between detectors D1'-D5'. The arc 22a' is bounded by detectors D1' and D5' and defines the detector array span. Arc 22b' is that portion of the detector ring which is outside the detector array.

In FIG. 6, the source assembly 20', produces an X-ray field defined by the fan pattern 20b having an apex 20c and outer, diverging boundaries 54 and 56 which define the included angle of the fan pattern which floods the scan circle 34'. As shown in FIGS. 5 and 7, the eclipsing shutter mechanism 28' acts to reduce the included angle of fan pattern 20b whenever the source approaches either terminus $S_i'$ or $S_f'$ of its cycle. This is desirable because the array of detectors on ring 22' does not entirely encircle the scan circle and if the width of the radiation field was not so restricted, unused radiation would pass through scan circle 34' and needlessly increase the patient dosage.

The eclipsing effect of the shutter 28' is accomplished by utilizing the epicyclic mechanism of FIG. 4. It should, of course, be understood that other drive mechanisms such as, by way of example, a d.c. motor servo drive may also be employed. In the illustrated embodiment, the included angle between the first detector D1' and the last detector D5' is 212°. The remaining arc 22b', 148° in the example, is outside the detector array. The shutter mechanism 28' is utilized to preclude the projection of any portion of the X-ray of fan pattern 20b through the scan circle if that portion of the field would fall outside the detector array, i.e., on arc 22b'.

With the arrangement shown in the FIGS. 5–7, a 60% rotation of shutter 28' is required for each 100% positive rotation of the geometric center B of source assembly 20' and shutter 28' about orbital path 20a. The geometric center B of the shutter moves from point $S_i'$ to point $S_f'$ on path 20a in the direction of arrow S during a scan cycle, and the shutter rotates in the opposite or negative direction as indicated by arrow T. As shown in FIG. 5, the leading edge 60' of the shutter aperture is on a straight line projecting from detector D1' to the center B of source assembly 20' for as long as a straight line projecting from detector D1' to the source intersects the scan circle 34'. Thus, a shutter imposed edge $E_L$ of fan pattern 20b is trained on detector D1' continuously for as long as the detector is in the data-taking portion of the scan cycle. There may be some minor deviation of the imposed edge $E_L$, which is in effect the same as the deviation of an individual slit in the rotating collimator described below. The portion of the fan pattern between the trailing edge 54 of the fan pattern and the shutter imposed edge $E_L$ is blocked by the shielding portion 64' of shutter 28' and does not pass through the scan circle 34'. This is desirable because this portion of the fan pattern would fall outside the detector array and would needlessly increase the patient's exposure to radiation.

As the geometric centers of the source and shutter traverse about their common orbital path 20a in the direction of arrow S (clockwise), the shutter 28 rotates about the center B in the direction indicated by arrow T (counterclockwise) 0.6° for every 1° of rotation of the center B along arc 20a'. The fan pattern width increases while continuously training the shutter imposed edge $E_L$ of the fan beam on the detector D1' for as long as the detector D1' is in the data-taking portion of the cycle, i.e., the scan circle is intermediate the detector D1' and the source 24. The fan pattern continues to widen until the entire fan pattern bounded by leading edge 56 and trailing edge 54, falls on the detector array. At this point, the shutter aperture is completely out of the path of the fan pattern emanating from source 24' and the entire fan pattern floods the patient scan circle 34'. This is desirable since the entire fan pattern falls on the detector array.

The source assembly 20' is shown at the mid-point $S_m'$ of its travel in FIG. 6. This is representative of the flooded scan circle wherein the leading edge 56 of the fan pattern 20b falls on detector D2' and the trailing edge 54 falls on detector D4'. As the source assembly 20' continues its movement, leading edge 56 of the fan pattern approached detector D5', the last detector in the array. Again, it is desirable to block any portion of the fan pattern which will fall outside the detector array span. At this point, illustrated in FIG. 7 trailing edge 62' of the shutter aperture has rotated into blocking relationship with the source and shields the leading edge 56 and a portion of the fan pattern 20b, training the shutter imposed edge $E_L$ on the last detector D5' for as long as the detector D5' is in the data-taking portion of the scan cycle. After the source has completed its orbital cycle by traversing to point $S_f'$, both the source and the shutter are returned to the initial position $S_i'$ of FIG. 5.

By utilizing the shutter mechanism 28', the source can be rotated through any portion of its orbital path without passing any radiation through the scan circle that does not ultimately fall on the detector array span.

Figure 8:
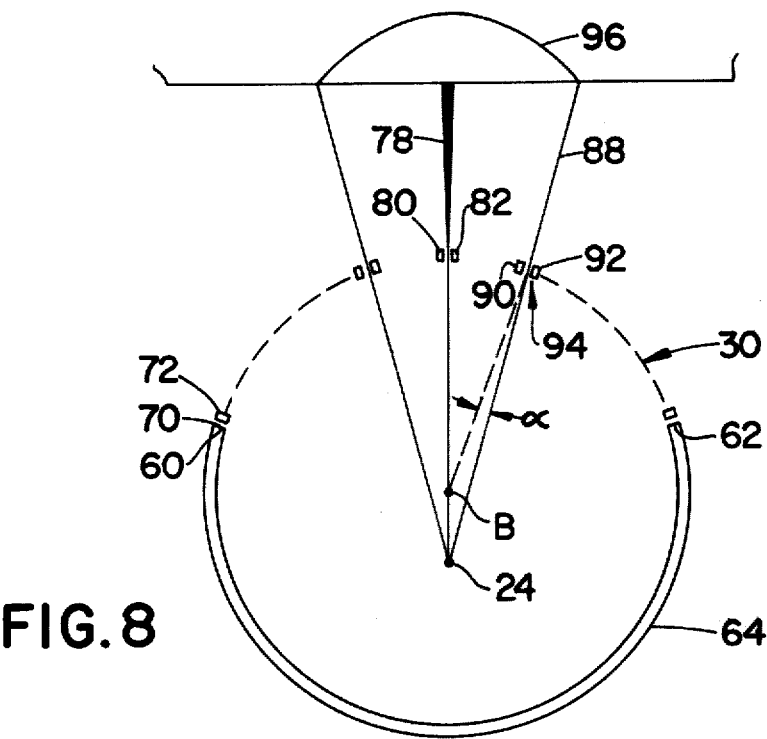
FIG. 8 is an enlarged view of a multi-apertured collimator.

Returning to the preferred embodiment of FIG. 2, the shutter assembly is shown in greater detail in FIG. 8. The section 30 of the shutter contains the same number of collimator apertures 70 as detectors—in the preferred embodiment 424. The apertures are defined by 423 radially disposed vanes 72. The vanes and apertures divide the fan 20b of radiation into finger beams of radiation. Further, source 24 is offset with respect to the geometric center B of the source assembly 20 and of the shutter mechanism. Accordingly, the orbital path 74 of source 24 is displaced from orbital path 20a of the source assembly.

Although each of apertures 70 has the same width, the radial orientation of the vanes 72 relative to shutter center B causes the apertures to present different effective aperture widths to source 24. For example, in forming a finger beam 78, which passes from source 24 through center B, vanes 80 and 82 which define an aperture 84 are oriented essentially radially toward source 24. Thus, the physical width of the aperture is the effective width of the aperture and the width of the finger beam it forms. However, for a finger beam 88, at the side of the fan, vanes 90 and 92 which define an aperture 94 are skewed with respect to source 24. The effective width of aperture 94 is smaller than the actual spacing of vanes 90 and 92. For the finger beam skewed by an angle $\alpha$ relative to orientation of the vanes, the effective aperture width, $W_{eff}$, is generally related to the actual physical width, $W_{phys}$, of the aperture:

$$W_{eff} = W_{phys} - l \sin \alpha$$

where l is the radial length of the vanes. Thus, the farther a finger beam is from central beam 78, the smaller the effective width becomes. The longer the radial dimension of the vanes, the more rapid the decrease.

The amount of radiation generated by source 24 is generally constant across the fan 20b. The amount of radiation in each finger beam is proportional to its cross-sectional area. For the preferred embodiment in which the beam thickness is constant, the amount of energy in each finger beam is proportional to the effective width of the collimator aperture which shaped it. A resulting energy distribution across the fan of finger beams is illustrated by curve 96. This distribution is generally like that produced with conventional attenuating filter elements. This same distribution can be achieved by varying the cross-sectional area of in other ways. For example, the thickness of the opening in shield 26 may be varied, thus varying the cross-sectional area by varying the thickness of the beams.

FIGS. 9, 10, 11 and 12 show progressive clockwise orientations of the source during rotation. As the source assembly rotates along arc 20a, and the source rotates along arc 74 as indicated by arrow S, the collimator rotates about center B, as indicated by arrow T. The ratios of the gears of FIG. 4 are chosen such that each collimator aperture will remain positioned between source 24 and a corresponding detector. For example, an aperture A1 defined by the leading edge 60 of shutter 28 and a first vane is, during the period of the scan in which radiation passes through A1, always between a first detector D1 and source 24.

For purposes of illustration, the collimator arc section 30 of the shutter is shown with five apertures A1, A2, A3, A4 and A5. Each aperture corresponds to one of detectors D1-D5.

Figure 9:
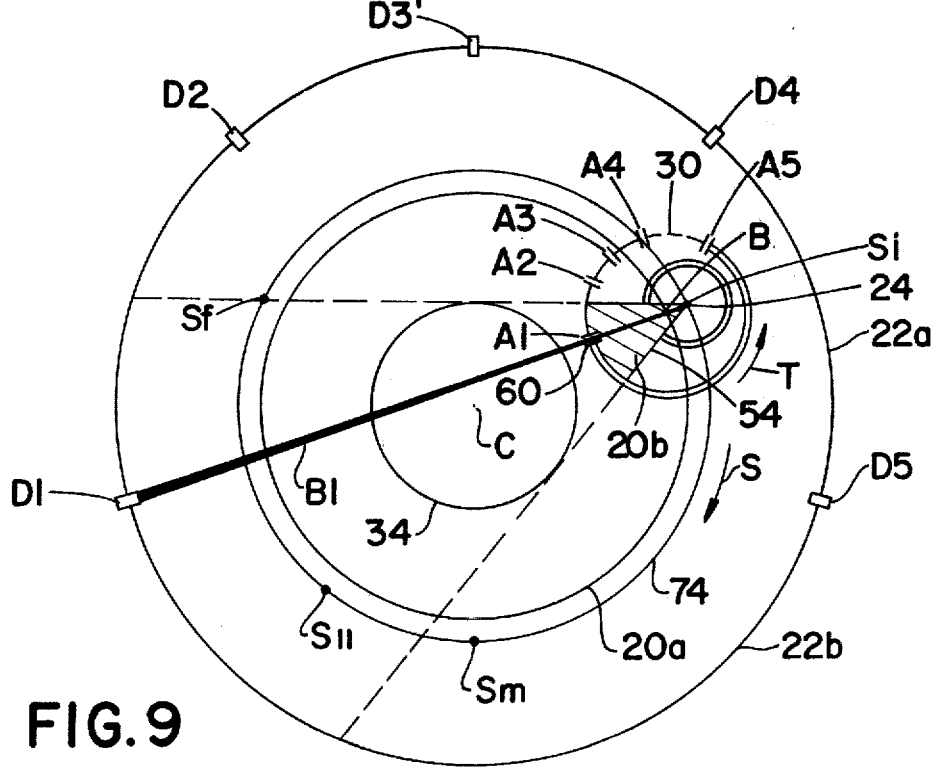
FIGS. 9, 10, 11 and 12 are schematic representations of the relative positions of the source, shutter mechanism with multi-apertured collimator, array of finger beams and detectors at four different orientations.

FIG. 9 corresponds to FIG. 5 in that the source assembly 20 is at initial point $S_i$. In this position, aperture A1, defined by leading edge 60 and the first vane, focuses a first beam B1 and detector D1. This beam is analagous to the shutter imposed edge $E_L$ of the fan beam in FIG. 5.

Figure 10:
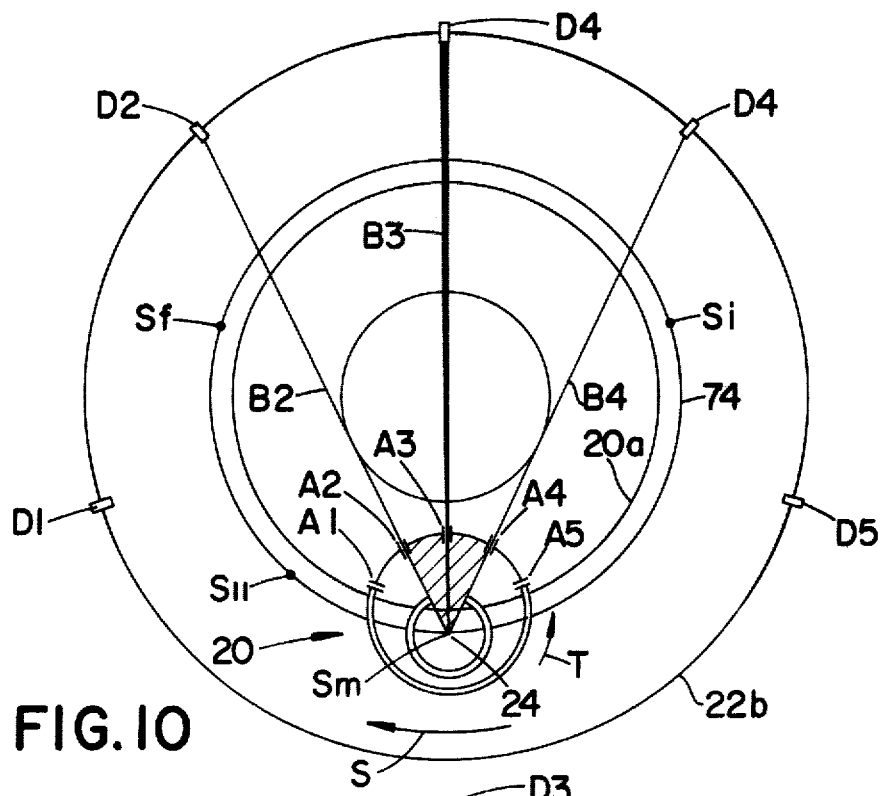

In FIG. 10, the source assembly 20 has rotated to mid-point $S_m$ analagously to FIG. 6. In this position, aperture A1 has passed out of the fan beam and apertures A2, A3 and A4 now define beams B2, B3 and B4, respectively. Beam B3, being at the center of the fan, has the greatest width; whereas, beams B2 and B4, being at the edge, have the least width.

Figure 11:
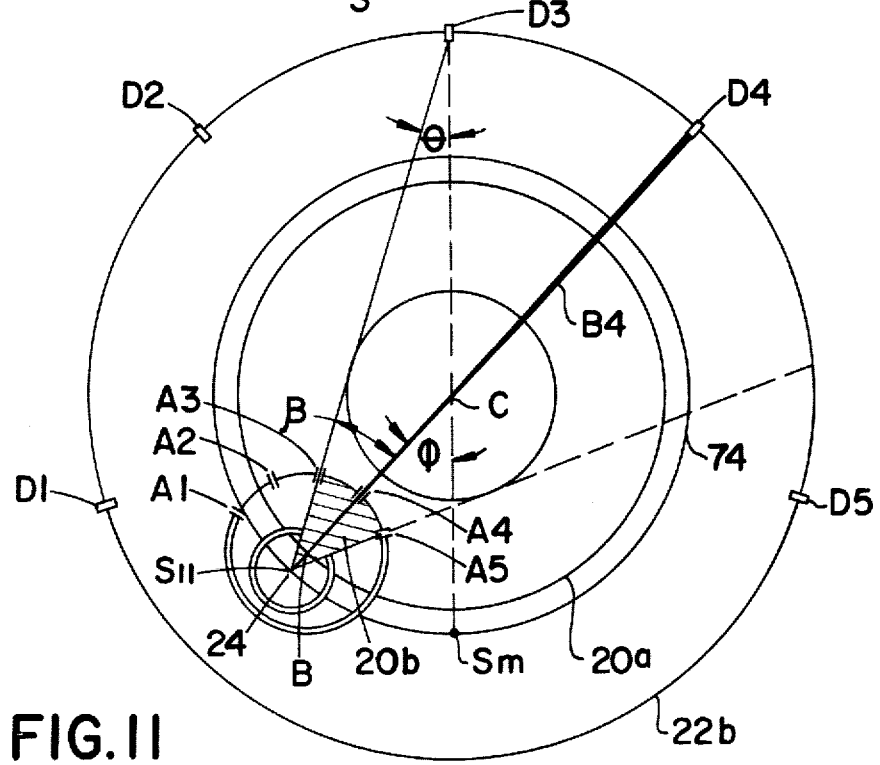

As the source sweeps from position $S_m$ in FIG. 10 to position $S_{11}$ in FIG. 11, beam B3 gradually diminishes in width. As the beam B3 shifts its relative location in the fan from the center in FIG. 10 to the edge in FIG. 11, its width decreases generally, parabolically as illustrated by curve 96 of FIG. 8. Analagously, as beam B4 shifts from the edge in FIG. 10 to the center in FIG. 11, its width increases parabolically.

Figure 12:
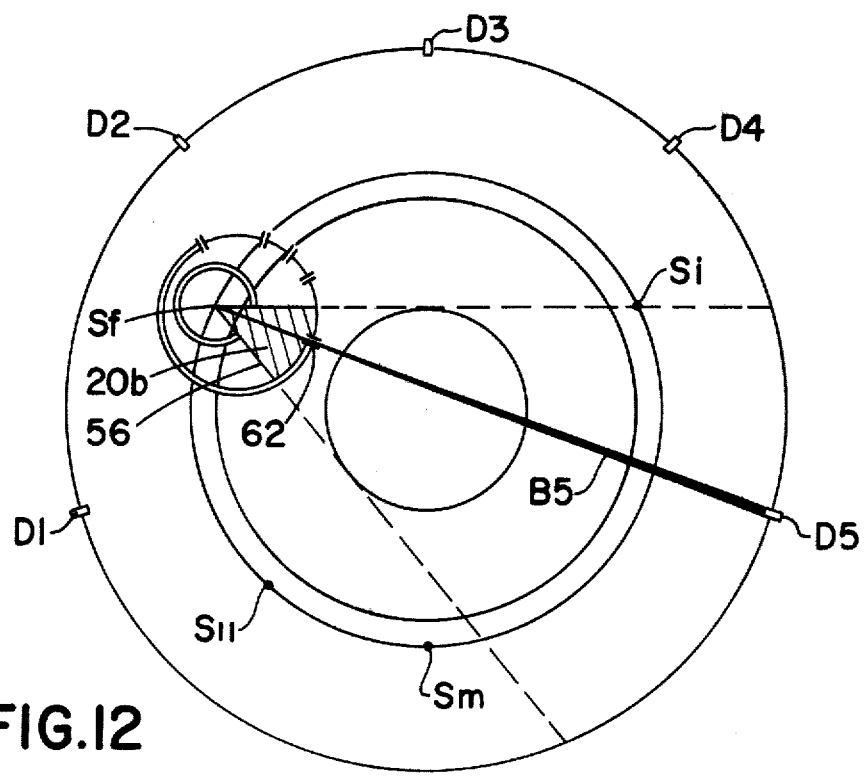

As the source continues to rotate from position $S_{11}$ to the final position $S_f$ in FIG. 12, beam B4 diminishes in width and is eliminated and a new beam B5 appears and widens.

To determine the gear ratio between the gears of FIG. 4, reference is again made to FIGS. 10 and 11. It will be seen that in rotating from point $S_m$ to $S_{11}$, source 24 rotates through an angle $\phi$ about the center of rotation C. Beam B3 shifting from the center of the fan beam to the edge to remain fixed on detector D3 shifts by an angle $\beta$. This angle $\beta$ is one-half the fan angle of fan 20b.

It will be appreciated that angle $\beta$ is less than angle $\phi$ because of the geometry of the source and detector arrangement. The ratio of the angular velocity of the source to the angular velocity of aperture A3 or any other aperture on the collimator is determined by the relationship between the radius of the source orbit 74 and the radius of the detector ring 22. It can be shown that there are values of these two radii at which the ratio of the angular velocities of the source about the center c and the collimator ring 28 can be accommodated by a reduction gear train. For example, it can be shown that if the detector ring has a radius of 36 inches and the source rotates around a radius of 26 inches, the angular velociy of the collimator should be 69.23% (in the opposite direction) of the angular velocity of the source about the center. This ratio of $-0.69$ for the angular velocities of the source and collimator is accomplished by the following gears, referring to FIG. 4: the sun gear 46 has 600 teeth; the larger compound gear 44 engaging the sun gear 46 has 104 teeth; the smaller compound gear 42 engaging the planetary gear 32 has 48 teeth and the planetary gear 32 has 400 teeth. The ratio of the number of teeth on the sun gear 46 to the number of teeth on the larger compound gear 44 multiplied by the ratio of the number of teeth on the smaller compound gear 42 to the number of teeth on the planetary gear 32 is 0.6923. Any other kind of epicyclic gear train that reverses the sense of rotation of the planetary gear and collimator ring 28, and provides a reduction of the above ratio will do. It also appears, because of the circular geometry of the system, that the dimensions of the radii of the source and detector ring will scale properly; that is, for a given ratio of the detector ring radius to the source radius the same angular velocity ratio for the collimator and source is required no matter what the size of the system.

Figure 13:
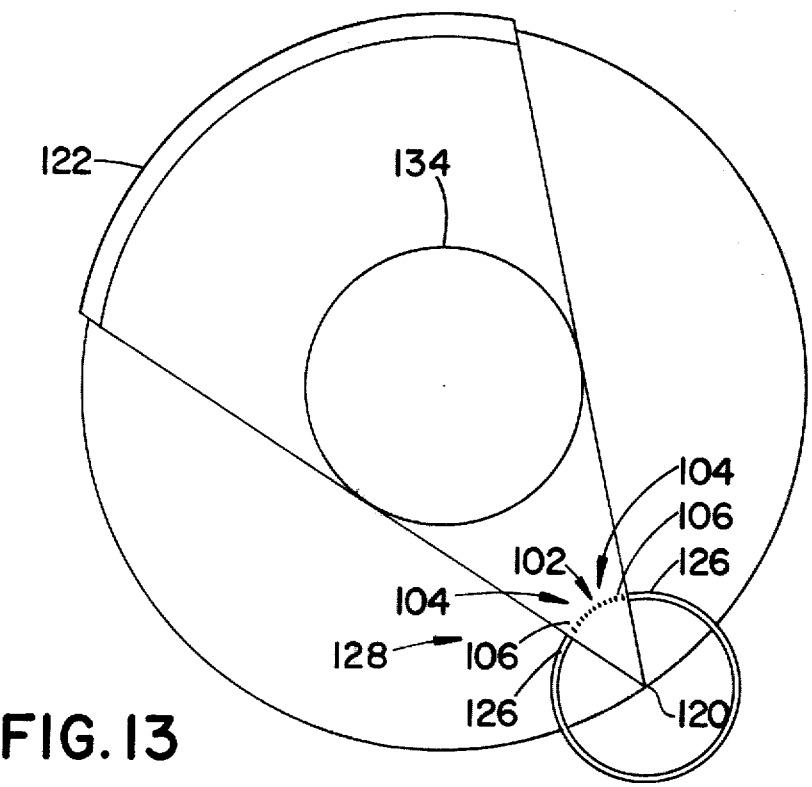
FIG. 13 is an alternate embodiment of a collimator-assembly in conjunction with a rotating source-rotating detector CT scanner.

Another embodiment of the present invention is shown in FIG. 13 in conjunction with a rotating source-rotating detector tomographic scanner. This embodiment includes a source 120 of a fan beam of radiation with sufficient spread to encompass scan circle 134. An arc of detectors 122 is mounted with source 120 for rotation about the scan circle. A collimator assembly 128 mounted for rotation with source 120 is comprised of a series of apertures. The apertures have a constant center-to-center spacing but vary in width such that the center aperture is widest and the edge apertures are narrowest. The effective width of the apertures may be varied as in the preceding embodiment by using constant width vanes skewed to varying degrees. Alternately, the apertures may be varied in width by varying the width of the radiation blocking material defining the apertures. In FIG. 13, the aperture defining material is a series of round rods or drawn wires. The rods are mounted with a constant center-to-center spacing. The central rod 102 has the smallest diameter, intermediate rods 104 a larger diameter, and the edge rods 106 the largest diameter.

As the source, collimator-assembly and detectors rotate, the finger beam nearest center of the scan circle is defined by rod 102 and a neighboring rod and the finger beams most nearly tangential to the scan circle are defined by rods 106 and a radiation shield 126 which limits the fan of radiation to the scan circle. By choosing the diameters of the rods appropriately, various bell curve-shaped and other radiation distributions can be created. This collimator assembly can be combined with the rotating source/stationary detector implementation of FIG. 3 by inserting rods in the opening of shield 26.

The present invention may also be used in conjunction with a traverse and rotate scanner. A collimater assembly may position between the traverse path of the source and the scan circle. It may be connected to the source to traverse with it or it may be connected with a cylinder surrounding the scan circle. As in the rotating fan beam embodiment, the collimator is designed to allow finger beams with a greater cross sectional area to traverse the center of the scan circle than the edges of the scan circle. This may be achieved with an array of skewed vanes, which present a wider effective aperture near the center of the scan circle. Alternately vanes or pins of varying width may be used or the thickness of the beam may be varied.

This invention has been described with reference to the preferred embodiments with some possible modifications thereto. Obviously, other modifications and alterations will be obvious to others upon the reading and understanding of this specification. It is our intention to include all such modifications and alterations insofar as they come within the scope of the appended claims or the equivalents thereof.

We claim:

1. A collimator and a source combination for a tomographic scanning apparatus having a scan circle for placement of an object to be examined, means for rotating the source of radiation around the scan circle in the plane of the scan circle, the combination comprising:
   a plurality of vanes positioned along a generally circular arc oriented radially toward the geometric center of the circular arc;
   said source being positioned eccentrically relative said geometric center, whereby the vanes divide the fan pattern of radiation into a plurality of widths.

2. A radiographic scanner comprising:
   a scan circle for receiving of an object to be examined;
   radiation detection means at least partially encircling the scan circle;
   a source of a fan pattern of generally continuous radiation, said source disposed to irradiate at least a part of said radiation detection means with radiation which has traversed the scan circle; and
   a collimator comprising a plurality of vanes, each of said vanes disposed radially relative to a geometric center and displaced from each other to form apertures therebetween, said collimator disposed with said geometric center displaced from said source.

3. The scanner as set forth in claim 2 wherein said scan circle has a geometric center and said source has a geometric center and wherein the geometric center of said scan circle, the geometric center of said source and the geometric center of the vane are disposed in a substantially linear relationship.

4. The scanner as set forth in claim 2 wherein said vanes are disposed along a generally circular arc segment.

5. The scanner as set forth in claim 4 wherein said source is mounted for rotational movement about said scan circle and said collimator is mounted for rotational movement about said source in a fixed relationship with rotational movement of the source about the scan circle.

6. A radiographic scanner comprising:
   a scan circle adapted to receive an object to be examined;
   a source of a fan pattern of generally continuous radiation, said source being mounted for rotational movement about the scan circle, in the plane of the scan circle;
   a radiation detector means for detecting radiation from the source which has traversed the scan circle, said detector means disposed at least partially encircling the scan circle; and
   a radiation shield at least a part of which is disposed in a circular arc segment in the plane of the scan circle and is disposed eccentrially about said source, said radiation shield having a plurality of apertures therein for collimating the fan pattern of radiation into a plurality of diverging finger beams.

7. The scanner as set forth in claim 6 wherein said radiation shield comprises a plurality of vanes disposed along and generally perpendicular to said circular arc segment, whereby the eccentric disposition of the radiation shield relative to the source causes the vanes to be skewed relative to radiation eminating radially from the source.

8. The scanner as set forth in claim 6 wherein the source, the geometric center of the scan circle and the geometric center of the circular arc segment of the radiation shield are disposed in a substantially linear relationship and wherein each of the plurality of apertures has substantially the same width dimension along the circular segement, whereby the eccentric placement of the radiation shield relative to the source causes apertures disposed between the source and the geometric center of the scan circle to present a relatively larger effective width to radiation eminating from the source and apertures disposed between the source and the scan circle away from the center to present a relatively smaller effective width to radiation eminating from the source.

9. A radiographic scanner comprising:
   a scan circle adapted to receive an object to be examined;
   a source of a fan pattern of generally continuous radiation said source being mounted for rotational movement about the scan circle;

a radiation detection means for detecting radiation from the source which radiation has traversed the scan circle, said detector means disposed at least partially encircling the scan circle; and a collimator mechanism for dividing the fan pattern of radiation into a plurality of divergent finger beams, the collimator mechanism comprising a radiation shield disposed between the source and the scan circle, said radiation shield having a plurality of apertures therein, the width of each finger beam being determined by the effective width of the corresponding aperture, the effective widths of said apertures being sized such that the finger beams have different widths with the finger beams of the widest width traversing the scan circle near its center and the finger beams of narrowest width traversing the scan circle near its periphery.

10. The scanner as set forth in claim 9 wherein the energy distribution of the finger beams across the scan circle is defined generally by a bell curve.

11. The scanner as set forth in claim 9 wherein said radiation shield defines a generally circular arc segment which is mounted eccentrically about said source.

12. A collimator mechanism for a tomographic scanner having a scan circle for placement of an object to be examined, a source of fan pattern of continuous radiation rotatable about the scan circle in the plane of the scan circle and a detector means at least partially encircling the scan circle in the plane of the scan circle, comprising:

an array of apertures positioned between the source and the detector means for dividing the fan pattern of continuous radiation into a fan pattern of corresponding finger beams of radiation, the width of each finger beam determined by the effective width of the corresponding aperture;

the improvement comprising sizing the effective widths of said apertures such that the finger beams have different widths with finger beams of the widest width traversing the scan circle near its center and the beams of the narrowest width traversing the scan circle near its periphery.

13. The collimator as set forth in claim 12 wherein said array of apertures is defined by a radiation shield means having said array of apertures therein.

14. The collimator as set forth in claim 13 wherein said radiation shield means comprises:

a plurality of rods mounted along an arcuate segment wherein adjoining rods define the aperture width.

15. The collimator as set forth in claim 14 wherein said arcuate segment is fixedly attached with said source for rotation about the scan circle therewith and wherein the rods defining apertures which divide the fan of radiation into finger beams which traverse the scan circle near its center are of smaller diameter than the rods defining apertures which divide the fan of radiation into finger beams which traverse the scan circle near its periphery.

16. The collimator as set forth in claim 12 wherein said array of apertures comprises:

a plurality of vanes radially mounted along an arcuate segment wherein adjoining vanes define aperture width.

17. The apparatus as set forth in claim 16 wherein said arcuate segment is circular with a geometric center and wherein said source of radiation is within the arcuate segment and offset from the geometric center whereby apertures defined by vanes more askew with respect to the source divide the fan of radiation into narrower finger beams than apertures defined by vanes more in line with the source.

18. The apparatus as set forth in claim 17 wherein said arcuate segment is rotatably mounted about said geometric center.

19. The apparatus as set forth in claim 18 wherein said detector means is a series of stationary detectors and further including means for training each one of said finger beams on a single one of the stationary detectors during rotation of the source.

20. The collimator as set forth in claim 19 wherein said training means includes means for causing a fixed amount of rotation of said arcuate segment in the opposite sense about the center for each angular unit of rotation of the source about the scan circle.

21. The collimator as set forth in claim 20 wherein the length of the arcuate segment spanned by all of the apertures is in the same proportion to the arc spanned by all the detectors as said fixed amount of rotation of the arcuate segment is to said angular unit of rotation.

22. The mechanism of claim 21 wherein said means for causing a fixed amount of rotation is a mechanical drive system powered by rotation of the source and connected to rotate said arc segment.

23. The mechanism of claim 22 wherein said drive system is a set of wheels making driving contact with each other.

24. The mechanism of claim 23, wherein said wheels are gears.

25. The mechanism of claim 24, wherein said gears comprise an epicyclic gear train providing a gear reduction ratio of 1 to −0.69 of the source rotation to the rotation of the arc segment about the center.

26. The mechanism of claim 24, wherein said gears comprise an epicyclic gear train including a planetary gear concentric with said geometric center and moving therewith to which the arcuate segment is fixed, a stationary ring-shaped sun gear concentric to the scan circle, a compound drive gear consisting of a first gear engaging the sun gear and a second gear fixed to the first gear engaging the planetary gear.

27. The system of claim 26, wherein the ratio of the number of teeth on the sun gear to the number of teeth on the first compound gear multiplied by the ratio of the number of teeth on the second compound gear to the number of teeth on the planetary gear is substantially 0.69.

* * * * *